United States Patent [19]

Sule

[11] Patent Number: 5,143,118
[45] Date of Patent: Sep. 1, 1992

[54] SOLENOID CONTROL VALVE

[76] Inventor: Akos Sule, 4 Gates Ave., Roseland, N.J. 07068

[21] Appl. No.: 656,240

[22] Filed: Feb. 14, 1991

[51] Int. Cl.⁵ .......................................... F16K 31/06
[52] U.S. Cl. .............................. 137/554; 251/129.08; 251/129.16; 251/7; 137/625.5
[58] Field of Search ............................ 137/554, 625.5; 251/129.08, 129.16, 7

[56] References Cited

U.S. PATENT DOCUMENTS

| | | | |
|---|---|---|---|
| 4,195,662 | 4/1980 | Gottel | 137/554 |
| 4,341,241 | 7/1982 | Baker | 137/554 |
| 4,386,626 | 6/1983 | Yamada et al. | 137/554 X |
| 4,784,178 | 11/1988 | Kasaya et al. | 137/554 |
| 4,813,443 | 3/1989 | Pounder | 251/129.08 X |
| 4,974,622 | 12/1990 | Rader | 251/129.15 X |

Primary Examiner—Arnold Rosenthal
Attorney, Agent, or Firm—Bernard Malina

[57] ABSTRACT

A solenoid control valve includes a solenoid housing which encloses a solenoid and an armature which is actuated by the solenoid in order to control the flow of fluid through the valve. Contact spring makes continuous electrical contact with the armature and the armature is electrically insulated from the valve except when the solenoid brings the armature into contact with a stop portion which is integrally formed in the body of the valve. Contact between the armature and the stop completes an electrical circuit between the sring contact, the armature and the valve body, thereby providing a precise electrical indication of the mechanical state of the valve without any degradation due to hysteresis or mechanical losses.

12 Claims, 6 Drawing Sheets

5,143,118

SOLENOID CONTROL VALVE

BACKGROUND OF THE INVENTION

With the development of genetic research and allied medical and biological instrumentation including applications such as liquid chromatography, there has developed a need for a means to dispense and control fluids in a manner which exceeds the precision capabilities of existing solenoid valves. This need stems from the requirement to control the flow of fluids in a complex manner and the need to control and dispense fluids such as genetic substances which can be manufactured only in extremely small quantities and at extremely high cost. Along with these critical requirements there is a need to provide a control valve which is not subject to contamination by the fluid being processed.

The increased application of computer technology to the control of fluid processes coupled with the above requirements for precision in the control of fluids leads to a requirement in which not only must the control valve be able to be controlled by a computer, but the state of the valve must be able to be sensed by the computer in a precise manner without errors due to mechanical losses, inertia or mechanical hysteresis.

The need for precision in the delivery of the fluids being processed results in requirements for precision in the construction of valves which exceed the capability of conventional control valves and also exceed the ability to construct a precision valve using known construction methods.

SUMMARY OF THE INVENTION

In accordance with the present invention, there is provided a solenoid control valve which includes a valve body and a solenoid housing which encloses a solenoid and an armature which is activated by the solenoid in order to control the flow of fluid through the valve. In the primary embodiment of the invention, the armature controls the flow of fluid by operating a diaphragm and a poppet which cooperates with a valve seat, which is formed in the valve body. The armature is mounted on an armature shaft which is made of a non-magnetic insulating material and which is slideably mounted in the solenoid housing.

A contact spring is mounted on the bobbin in the solenoid and the contact spring makes continuous electrical contact with the armature throughout the entire range of motion of the armature. The armature is insulated from the solenoid housing and the valve body except at the end of its travel when the solenoid brings the armature to rest against a stop which is integrally formed in the solenoid housing. When the armature makes contact with the stop an electrical circuit is completed between the spring contact, the armature and the solenoid housing stop, thereby providing a precise independent electrical indication of the exact mechanical state of the solenoid operated control valve.

The completion of this electrical circuit can be used as part of a closed loop feedback control system to both report on and control the operation of the solenoid control valve. The electrical signal which results from the closure of this electrical circuit provides an extremely high degree of valve precision since there is no degradation due to mechanical hysteresis or other losses.

In an alternative embodiment of the invention the armature controls the flow of fluid through the valve by operating a plunger which bears on a flexible tube in order to prevent flow through the tube responsive to the operation of the solenoid.

OBJECTS OF THE INVENTION

It is an object of the present invention to provide a solenoid control valve which is capable of an extremely high degree of precision in controlling fluid flow.

Another object of the present invention is to provide a solenoid control valve which is capable of sensing the mechanical state of the valve in an extremely precise manner.

Another object of the present invention is to provide a solenoid control valve which is adapted for operation in a closed loop feedback system.

Another object of the present invention is to provide a solenoid control valve which is capable of indicating its response time in an accurate manner.

Another object of the present invention is to provide a solenoid control valve where on and off cycle times can be varied automatically.

Another object of the present invention is to provide a solenoid valve where cycle time can be adjusted in a continuous manner in response to the actual performance of the valve.

Another object of the present invention is to provide a solenoid control valve the accuracy of which can be controlled by a computer program.

Still another object of the present invention is to provide a solenoid valve which is capable of highly reliable operation over an extremely long useful life.

BRIEF DESCRIPTION OF THE DRAWINGS

Additional objects and a fuller understanding of the present invention may be had by referring to the present invention in which.

DETAILED DESCRIPTION OF THE INVENTION

Figure 1:
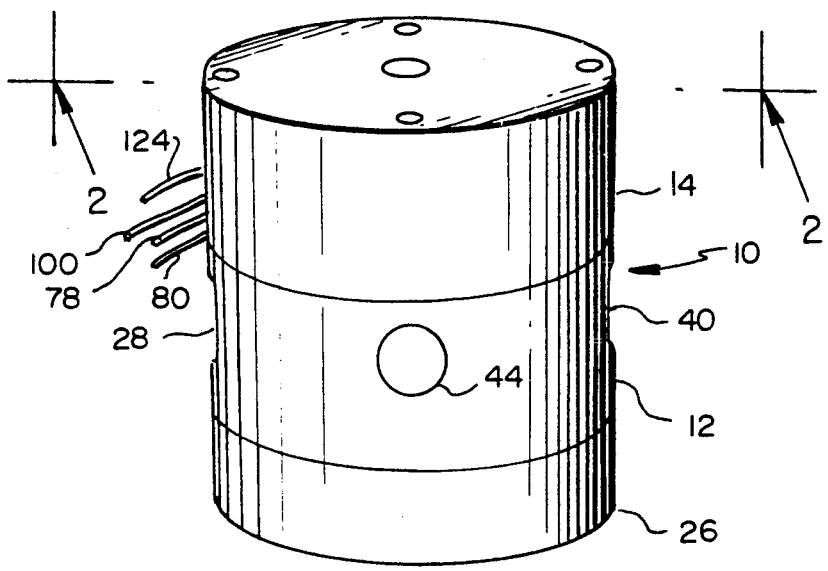
FIG. 1 is an overall perspective view of a solenoid control valve made in accordance with the present invention.

With reference to the drawings there is shown a solenoid control valve 10 made in accordance with the present invention which comprises a valve body 12, a solenoid housing 14, a solenoid coil assembly 16, an armature 18, a top plate 20, a shaft 22, a diaphragm assembly 24, and a base plate 26.

The valve body 12 includes a first port 28, which communicates with a first conduit 30. The first conduit 30 communicates with a valve cavity 32. The valve cavity 32 includes a pair of valve seats 34, 36 and communicates with a second conduit 38 which in turn communicates with a second port 40. The valve cavity 32 also communicates with a third conduit 42 which is shown in broken lines and which leads to a third port 44.

The diaphragm assembly 24 includes a first diaphragm 46 which has an integrally formed first sealing lip 48 and a centrally disposed first poppet 50 and a second diaphragm 52 which has an integrally formed second sealing lip 54 and a centrally disposed second poppet 56.

The end 58 of the shaft 22 which is made of an electrically insulating non-magnetic material bears on the first diaphragm 46. The end 60 of the shaft 22 is connected to the armature 18 which is made of an electrically and magnetically permiable material. A helical compression spring 62 bears on a spring plunger 64 which, in turn, bears on the second diaphragm 52, thereby urging the second poppet 56 against the second valve seat 36 while simultaneously lifting the first poppet 50 away from the first valve seat 34.

The bobbin 66 which is a part of the solenoid coil assembly 16 includes a top flange 68, a bottom flange 70, and a central core 72. A solenoid coil 74 is wound on the central core 72 in the space 76 defined by the central core 72 and the top and bottom flanges 68, 70. The solenoid coil leads 78, 80 are brought out of the solenoid housing 14 via the aperture 82. The bobbin 66 is retained in the solenoid housing 14 by means of a retaining spring 84 which rests in a groove 86 formed in the solenoid housing 14.

A contact spring 88 is mounted on the upper surface 90 of the top flange 68 of the bobbin 66 and is retained in place by a pair of integrally formed projections 92, 94 which project into an aperture 96 formed in the top flange 68 and are then flared outwardly. The contact spring 88 is generally semi-circular in configuration and includes a tab portion 98 on to which a lead 100 is connected. The contact spring 88 is formed so that the upper surface 110 of the contact spring 88 is continuously in contact with the bottom surface 112 of the armature 18 throughout the entire range of motion of the armature 18.

An insulating disk 114 is positioned above the armature 18 between the armature 18 and the top plate 20, thereby electrically insulating the armature 18 from the top plate 20. The insulating disk 114 may be made of Mylar or any similar thin sheet plastic material which has good electrical insulating properties. The armature 18 is mounted on the shaft 22 which, as previously indicated, is also an electrical insulator and consequently the armature 18 is completely insulated from the solenoid housing 14 except in the critical manner which will be presently described.

Figure 2A:
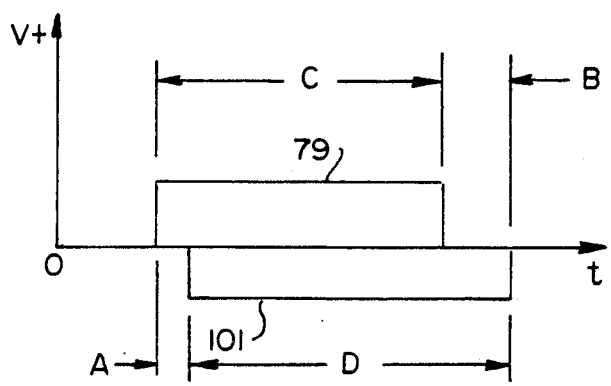
FIG. 2A is a graph showing the time relationship between the voltage applied to the solenoid and the mechanical response of the solenoid.
Figure 2:
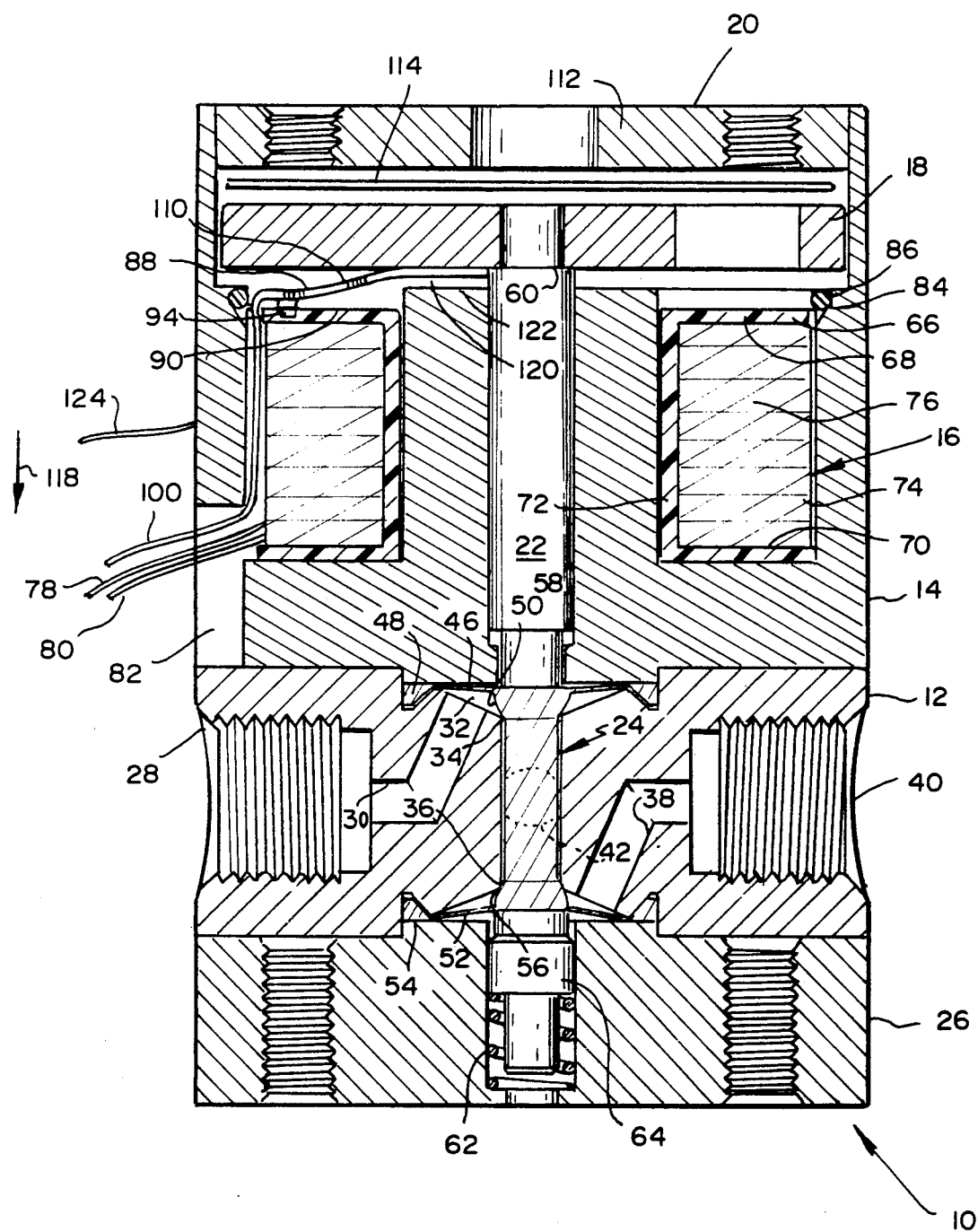
FIG. 2 is a cross-sectional view taken along the line 22 of FIG. 1.

When the solenoid coil 16 is energized, the armature 18 moves downward in the direction indicated by the arrow 118 in FIG. 2 until the bottom surface 112 rests against the surface 120 of an armature stop portion 122 which is integrally formed in the solenoid housing 14. When the armature 18 moves downward, the top poppet 50 is urged against the top valve seat 34 and the bottom poppet 56 is pushed away from the bottom valve seat 36 and contact between the armature 18 and the solenoid housing 14 completes a circuit between the lead 124 which is connected to the solenoid housing 14 and the lead 100 which is connected to the contact spring 88. When the solenoid coil 16 is deenergized, the helical spring 62 bears on the spring plunger 64 and forces diaphragm assembly 24 and thereby the armature 18 away from the armature stop portion 122, thereby breaking the electrical connection between the leads 100, 124. The helical spring 62 forces the armature 18 toward the top plate 20. However, the insulating disk 114 prevents electrical contact between the armature 18 and the top plate 20.

The action of the armature 18 to make and break the electrical circuit formed by the leads 100, 124 provides a precise electrical indication of the mechanical position of the solenoid control valve 10. This electrical indication of the mechanical position of the solenoid control valve 10 is provided without a need to resort to external sensor assemblies, sliding contacts or other devices which are subject to errors caused by mechanical hysteresis and wear.

This electrical signal can be fed to a computer control system which can provide a feedback signal to the solenoid coil 16 in order to energize the coil when fluid flow through the solenoid coil is required and deenergize the solenoid coil 16 when no fluid flow is required. Because the electrical signal is an exact indication of the mechanical state of the valve 10, a highly precise feedback type control of the fluid flow can be achieved.

The extreme accuracy of this electrical signal as a measure of the mechanical position of the valve facilitates the use of this signal in a manner which results in valve accuracies which cannot be achieved using conventional valve systems. The electrical signal can, for example, be used to compensate for the small amounts of wear which can occur over time thereby providing accuracy of operation for extended periods. This signal can also be used to compensate for changes which occur as a result of changes in environmental conditions such as heating of the solenoid coil 16 which increases the electrical resistance or environmental conditions which change the properties of the fluid.

The extreme accuracy of the electrical signal as a measure of the mechanical position of the valve facilitates the computer control of the valve through the adjustment of the cycle-time as a function of the valve position. The computer control of the valve can achieve continuous adjustment of various parameters of the valve by adjusting the voltage applied to the solenoid.

Referring to FIG. 2A, curve 79 represents the voltage applied to the solenoid at leads 78, 80, and curve 101 indicates the generated signal across leads 100 and 124 representing the actual mechanical response of the valve. Thus, C represents the time period that the solenoid is energized, while D represents the time period during which valve is actually open. Thus, time period A represents the ON response time and B the OFF response time. Since delay periods A and B are generally unequal due to hysteresis, pulse widths C and D will also be unequal. Accordingly, the actual valve operating period D is selectively variable by adjusting C according to the relationship $D = C + B - A$. Since periods A and B are readily measured by a computer (not shown), the desired value of period D is thereby easily achieved by selectively varying period C.

The foregoing ability of the control valve of the present invention to accurately control periods of operation of valves is of great importance in analytical chemistry applications such as processes involving the measurement and dispensing of chemical reagents or DNA sequencing and synthesis. The adjustment may be made in response to any desired software algorithm or any desired set of inputs or signals which measure the characteristics of the fluid or process being controlled.

The application of the present invention has thus far been described in connection with a solenoid valve 10 in which the fluid is controlled by a pair of diaphragms 46, 52, each of which has a poppet 50, 56 which cooperates with a valve seat 34, 36. It is clear that the present invention can be applied to the entire range of solenoid operated diaphragm valves in which one or more diaphragms are operated by one or more solenoids.

It is also clear that the present invention can be applied to solenoid operated valves in which a solenoid operates a plunger which bears on a flexible tube causing the tube to collapse, thereby preventing fluid flow through the tube.

Valves of this type are described in my U.S. Pat. No. 4,496,133 and the details of construction of such valves have therefore not been included herein except as required for the description of the second embodiment of the present invention.

Figure 6:
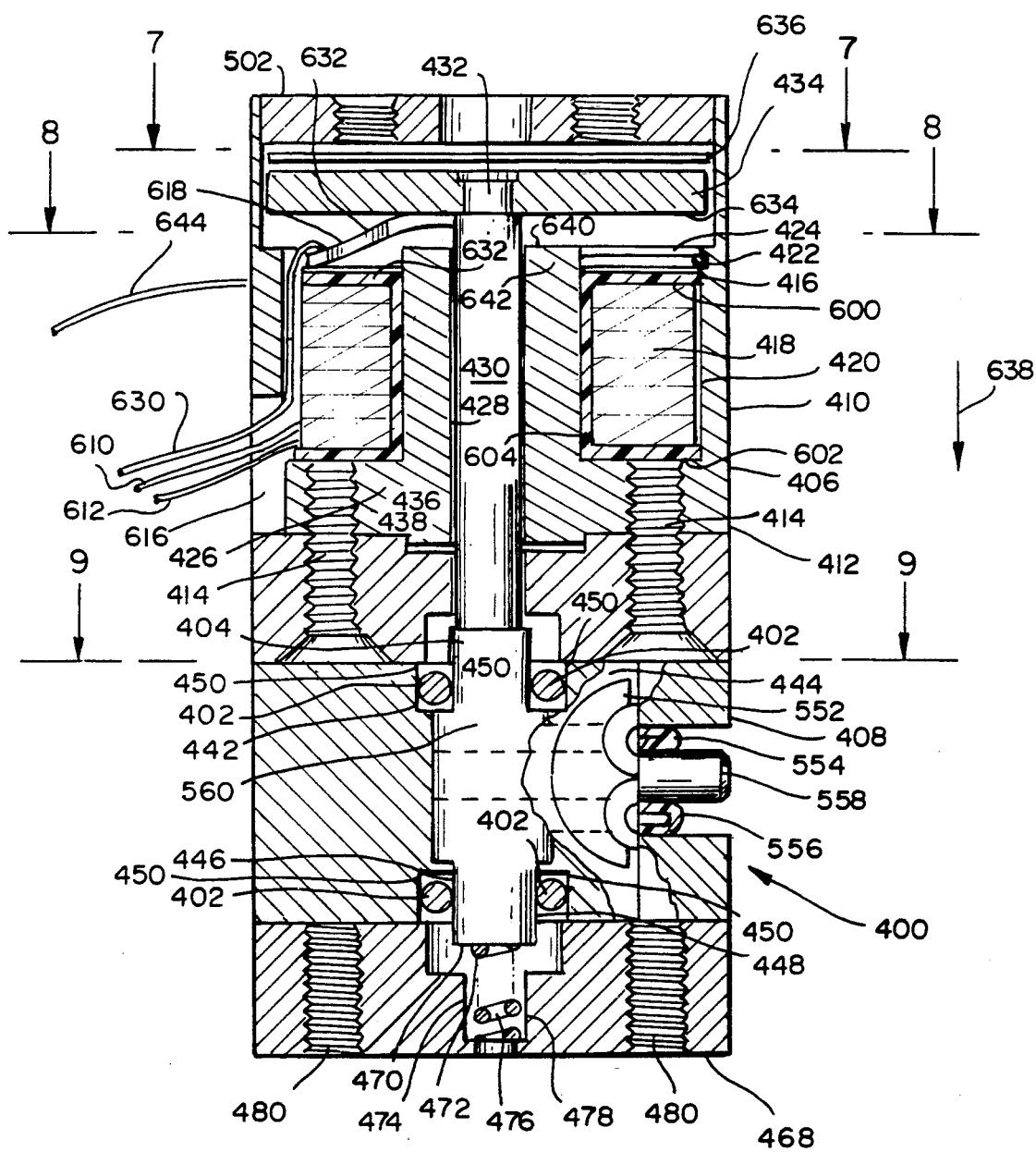
FIG. 6 is a cross-sectional view of a second embodiment of the invention.
Figure 7:
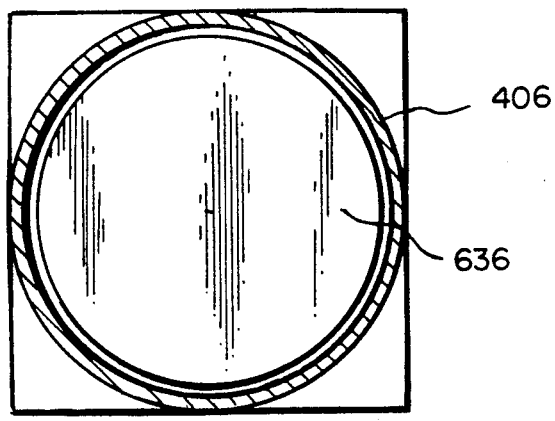
FIG. 7 is a cross-sectional view taken along the line 7—7 of FIG. 6.
Figure 8:
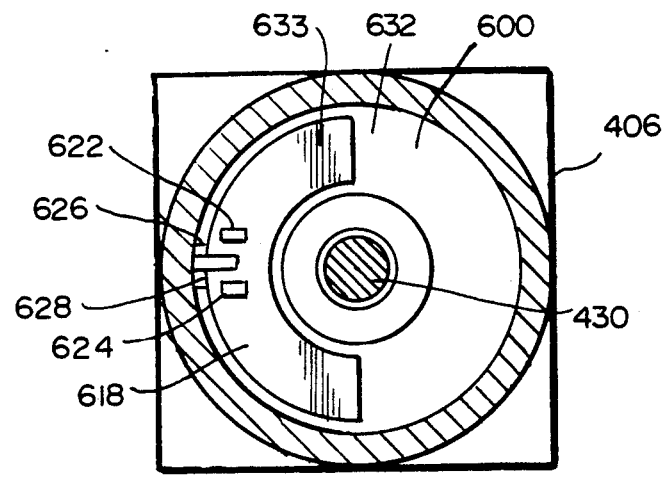
FIG. 8 is a cross-sectional view taken along the line 8—8 of FIG. 6.

In the second embodiment of the invention, shown in FIG. 6, the solenoid control valve 400 comprises a hollow solenoid housing 406 which is mounted on a valve body 408 in a conventional manner which is not shown.

The solenoid housing 406 comprises an upper portion 410 and a lower portion 412 which are connected by means of a pair of screws 414.

A solenoid bobbin 416 and a solenoid coil 418 are mounted in a cavity 420 formed in the solenoid housing 406 and are held in place by a retainer spring 422 which is lodged in a groove 424. The solenoid housing 406 includes a central hub portion 426 which has a central bore 428. An armature shaft 430, which is made of a non-conductive and non-magnetic material, slides within the central bore 428 and the upper portion 432 of the armature shaft 430 is press fit into an armature 434 which is made of a magnetic and electrically conductive material. The lower end 436 of the armature shaft 430 rests on the top surface 438 of the plunger 404. The plunger 404 includes two upper step portions 442, 444 and two lower step portions 446, 448, the function of which will be presently described. The plunger 404 rides within aligned cavities 450 respectively containing cylindrical roller pins 402 which bear on flat surfaces 403 and 405 and guide the plunger 404.

Figure 9:
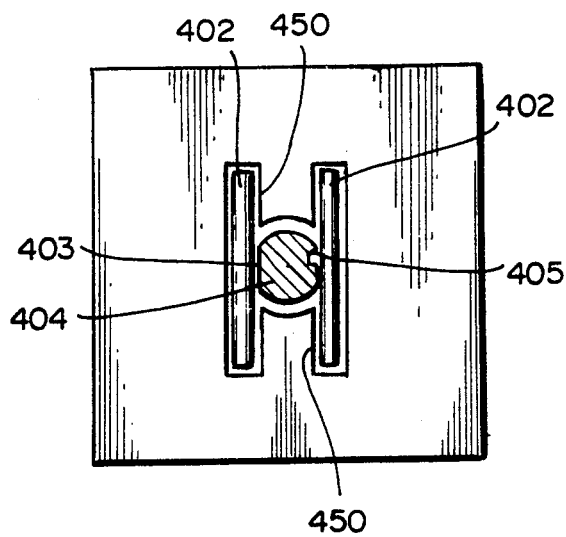
FIG. 9 is a cross-sectional view taken along the line 9—9 of FIG. 6.
Figure 10:
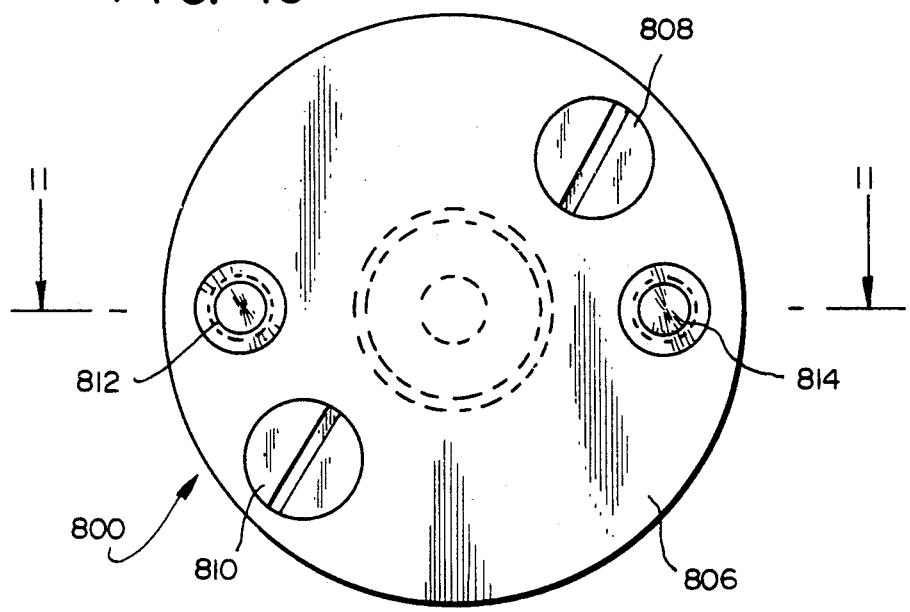
FIG. 10 is a bottom view of another embodiment of the invention showing a normally closed valve.

The cavities 450 are respectively proportioned to retain the four roller pins 402 as is shown in FIGS. 6 and 9.

The lower surface 470 of the plunger 404 rests on the upper end 472 of a helical compression spring 476. The lower end 478 of the spring 476 rests in a bore 474 which is formed in the bottom plate 468. The bottom plate 468 includes a pair of threaded holes 480 which may be used to mount the valve 400 in a selected location.

The tube retainer 552 holds a pair of flexible tubes 554, 556 and the pressure pin 558 projects only from one side of the plunger portion 560. The roller pins 402 enable the plunger portion 560 to move freely even though it is subjected to an unbalanced load caused by the pressure pin 558 and the flexible tubes 554, 556 being on only one side of the plunger.

In the embodiment 400 shown in FIG. 6, the flexible tube 554 is normally closed, and is held closed by the action of the spring 476 which bears on the plunger portion 560. When the solenoid coil 418 is electrically energized, the armature 434 is drawn toward the solenoid coil 418 overcoming the force of the spring 476, allowing the flexible tube 554 to open and forcing the flexible tube 556 closed.

In a manner similar to that which has been described in connection with the primary embodiment of the invention, the bobbin 416 includes a top flange 600, a bottom flange 602, and a central core 604. The solenoid coil 418 is wound on the central core 604 in the space defined by the central core 604 and the top and bottom flanges 600, 602. The solenoid coil leads 610, 612 are brought out of the solenoid housing 406 via the aperture 616.

A contact spring 618 is mounted on the upper surface 632 of the top flange 600 of the bobbin 416 and is retained in place by a pair of integrally formed projections 622, 624 which project into an aperture 626 formed in the top flange 600 and are then flared outwardly. The contact spring 618 is generally semicircular in configuration and includes a portion 628 onto which a lead 630 is attached. The upper surface 633 of the contact spring 618 is continuously in contact with the bottom surface 634 of the armature 434 throughout the entire range of motion of the armature 434.

An insulating disk 636 is positioned above the armature 434 between the armature 434 and the top plate 502, thereby electrically insulating the armature 434 from the top plate 502. The insulating disk 636 may be made of Mylar or any similar thin sheet plastic material which has good electrical insulating properties. The armature 434 is mounted on the armature shaft 430 which as previously indicated is also an electrical insulator and consequently the armature 434 is completely insulated from the solenoid housing 406 except in the critical manner which will be presently described.

When the solenoid coil 418 is energized, the armature 434 moves downward in the direction indicated by the arrow 638 in FIG. 6 until the bottom surface 634 rests against the top surface 640 of an armature stop portion 642 which is integrally formed in the solenoid housing 406.

An electrical lead 644 and contact between the armature 434 and the solenoid housing 406 completes a circuit between the lead 644 which is connected to the solenoid housing 406 and the lead 630 which is connected to the contact spring 618. When the solenoid coil 418 is deenergized, the helical spring 476 forces the armature 434 away from the armature stop portion 642, thereby breaking the electrical connection between the leads 630, 644. The helical spring 476 forces the armature 434 toward the top plate 502 however, the insulating disk 636 prevents electrical contact between the armature 434 and the top plate 502.

The action of the armature 434 to make and break the electrical circuit formed by the leads 630, 644 provides a precise electrical indication of the mechanical position of the solenoid control valve 400. This electrical indication of the mechanical position of the solenoid control valve 400 is provided without a need to resort to external sensor assemblies, sliding contacts or other devices which are subject to errors caused by mechanical hysteresis, dirt, wear or contamination.

A third embodiment of the invention 800 is shown in FIGS. 10, 11, 12, 13. Valves of this type are described in my U.S. Pat. No. 4,711,269 and the details of construction of such valves have therefore not been included herein except as required for the description of the third embodiment of the present invention.

The embodiment 800 is a normally closed solenoid valve which comprises a valve body 802 which is mounted between a top plate 804 and a bottom plate 806 by means of two machine screws 808, 810 which engage tapped holes in the top plate 804. The bottom plate 806 also includes two tapped holes 812, 814 which may be used to mount the solenoid valve 800 in a desired location. The valve body 802 and the top 804 and bottom plates 806 are each generally cylindrical in configuration.

Figure 11:
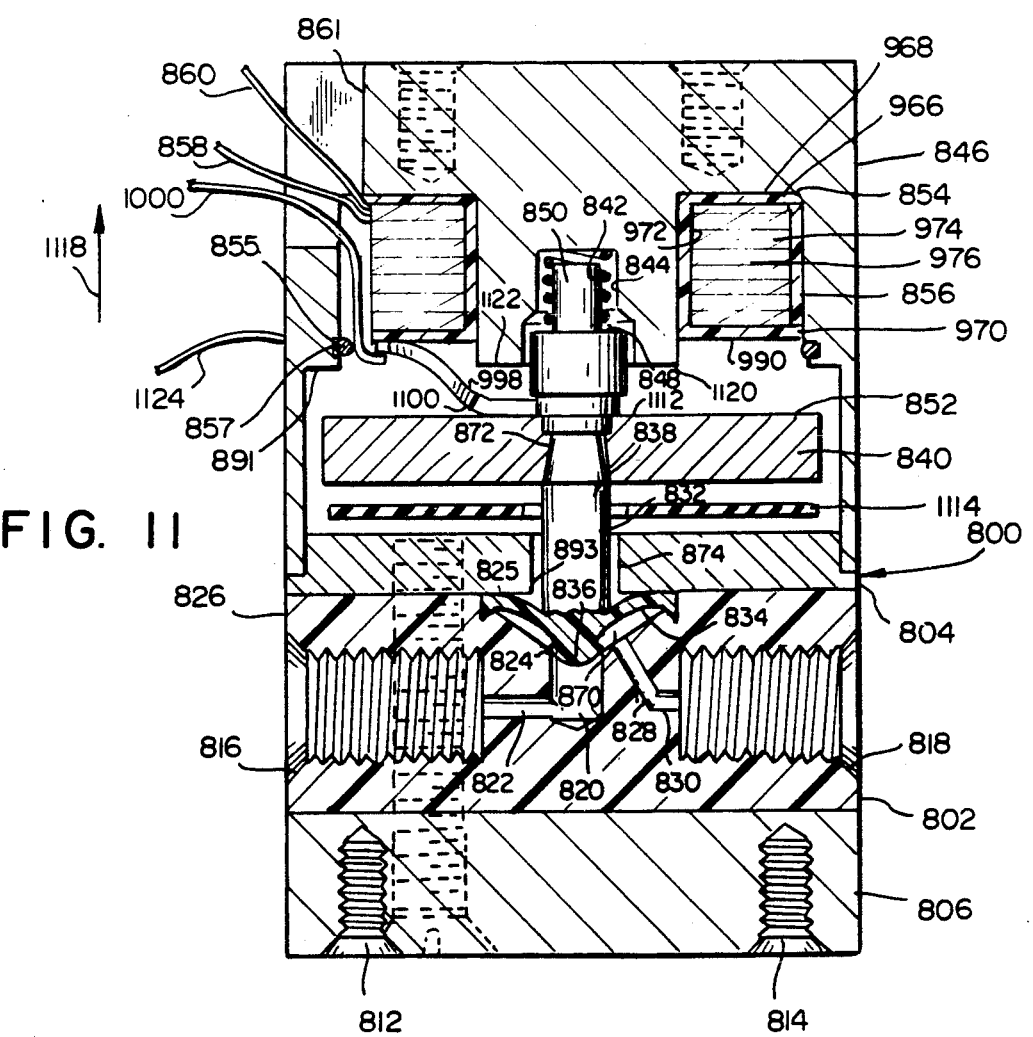
FIG. 11 is a cross-sectional view, taken along the line 11—11 of FIG. 10, with the valve shown in the closed position.
Figure 12:
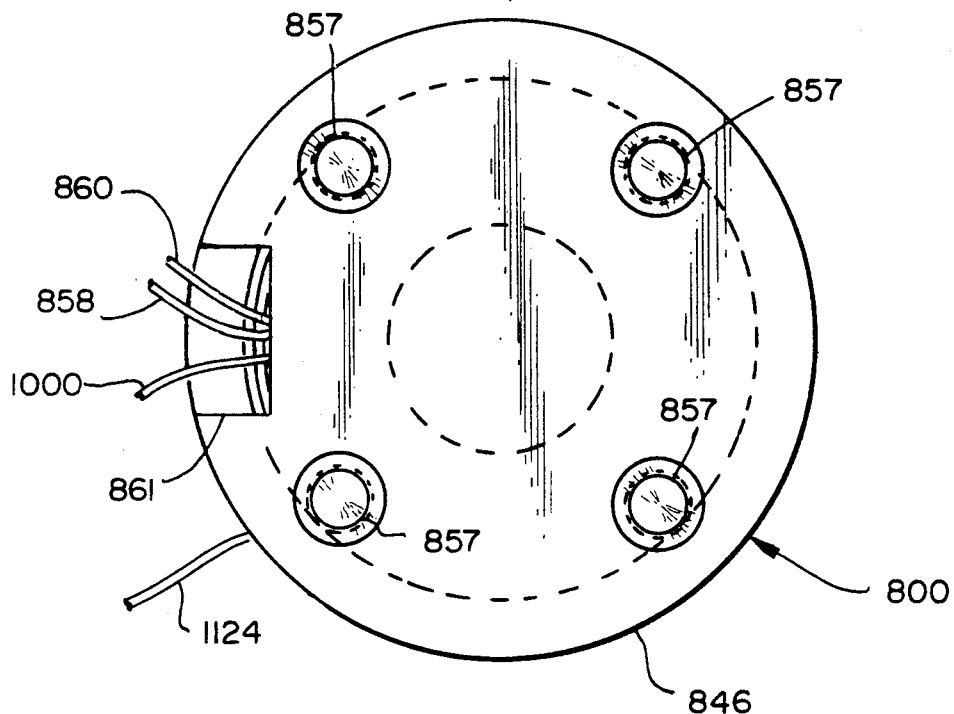
FIG. 12 is a top view of the embodiment of FIG. 10.

The valve body 802 includes a left port 816 and a right port 818. The designations left port 816 and right port 818 relate to the orientation of the solenoid valve assembly 800 as shown in FIG. 11 and these designations have been made only as a matter of convenience. The left port 816 communicates with a central bore 820 via a conduit 822. The central bore 820 communicates with a valve cavity 870 which is formed in the upper portion 826 of the valve body 802.

The right port 818 communicates with the valve cavity 870 by means of an angled conduit 828 which leads to a horizontal conduit 830. Valve seat 824 is formed by the intersection of tapered portion 825 of valve cavity 870 and central bore 820.

A diaphragm member 832 is provided which includes a diaphragm portion 834, a poppet portion 836, and a shaft portion 838. The shaft portion 838 is made of an electrically insulating material and is connected to an armature disk 840 in a manner which will be presently described. The armature disk 840 is urged downward by a helical spring 842 which is lodged in a cavity 844 formed in a solenoid housing 846 which is mounted on the top plate 804. The lower end 848 of the helical spring 842 bears on a spring seat member 850 which in turn bears on the top 852 of the armature disk 840. The downward motion of the armature disk 840 causes the poppet portion 836 to come into contact with the valve seat 824 thereby preventing flow between the left 816 and right 818 ports and closing the solenoid valve 800. The solenoid valve 800 remains in the closed position until a solenoid coil 854 which is lodged in a cavity 856 in the solenoid housing 846 is electrically energized via the leads 858, 860, thereby drawing the armature disk 840 upward and moving the poppet portion 836 away from the valve seat 824. The solenoid coil 854 is held in place by a retaining spring 855 which is lodged in a groove 857 formed in the solenoid housing 846. The leads 858, 860 pass through an aperture 861 which is formed in the solenoid housing 846. The solenoid housing 846 also includes four tapped holes 859 shown in FIG. 12 which may be used to mount the solenoid valve 800 in a desired location.

Figure 13:
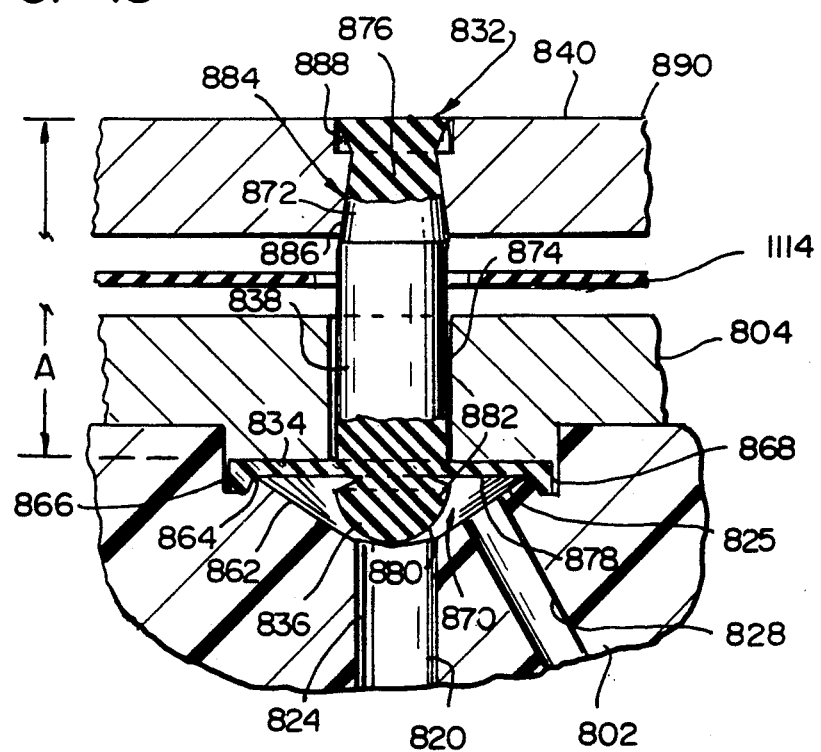
FIG. 13 is a fragmentary cross-sectional view similar to FIG. 11 drawn to an enlarged scale, showing details of internal construction with the valve shown in the open position.

The valve seat 824 and the diaphragm member 832 are best shown in FIG. 13 and the valve cavity 870 comprises a conical portion 862 which communicates with the central bore 820. The outer edge 864 of the conical portion 862 leads to a V-shaped groove 866 which is formed in the valve body 802. The groove 866 accepts a V-shaped lip 868 which is formed on the diaphragm portion 834. The shape of the valve cavity 870 in combination with the diaphragm member 832, which will be presently described in detail, reduces the internal volume of the cavity 870 of the solenoid valve 800 and increases the reliability of the valve by increasing the contact area between the poppet portion 836 and the valve seat 824, thereby reducing the contact stress and improving the useful life of the unit. Furthermore this design serves to reduce the degree of deformation of valve seat 824 during operation of the valve.

As is best shown in FIG. 13, the shaft portion 838 of the diaphragm member 832 projects upward from the diaphragm portion 834 and includes an inwardly tapered portion 872. The shaft portion 838 passes through a clearance hole 874 formed in the top plate 804 and the upper portion 876 of the shaft is connected to the armature 840. The poppet portion 836 projects downward from the lower surface 878 of the diaphragm disk 834 and includes a spherical portion 880. The poppet portion 836 also includes a conical undercut 882 formed at the intersection between the poppet portion 83 and the diaphragm disk 834.

The diaphragm member 832 is made of a plastic material having the required properties of strength, flexibility, and toughness. A plastic material which has been found to possess the required combination of physical properties is sold under the tradename Teflon. Other materials having these required properties may also be used.

The diaphragm portion 834 is deformed in the closed position and the diaphragm portion 834 leaves the top plate 804 to the extent of the movement of the poppet portion 836. FIG. 13 shows the solenoid valve 800 in the open position. In the open position, the diaphragm portion 834 is undeformed and is fully in contact with the top plate 804.

The armature 840 has a central bore 884 which includes an inwardly tapered portion 886 and a counterbored portion 888. The inwardly tapered portion 886 of the bore 884 and the tapered portion of the shaft 838 are proportioned so that, when assembled, there is a force fit between the armature 840 and the shaft 838. During assembly, the tapered upper end 876 of the shaft 838 is introduced into the inwardly tapered portion of the bore 884 and the armature 840 is pressed downward onto the shaft 838 until a critical height is reached. This critical height is a preselected precise dimension as described below between the diaphragm portion 834 to the top of the armature 840. This dimensional relationship is shown as the reference letter A in FIG. 13. As the armature 840 is pressed onto the shaft 838, the shaft portion 876 is compressed. The shaft portion 876 which is in the area of the counterbored portion 888, having been compressed by the tapered portion of the armature 840, expands into the counterbored portion 888, thereby locking the shaft portion 838 and the armature 840 together. The top of the shaft is then cut off flush with the top 890 of the armature 840.

The armature 840 and the diaphragm member 832 thus form a simple and reliably connected assembly which is easily assembled to form a preselected precise dimensional relationship between the diaphragm portion 834 and the top 890 of the armature 840. The dimension A in FIG. 13 is set during assembly to be identical to the distance between the surface 891 on the solenoid housing 846 and the surface 893 on the top plate 804. This allows the full amount of travel of the diaphragm member 832 and the poppet portion 836.

The bobbin 966 which is a part of the solenoid coil 854 includes a top flange 968, a bottom flange 970, and a central core 972. A solenoid coil 974 is wound on the central core 972 in the space 976 defined by the central core 72 and the top and bottom flanges 968, 970.

A contact spring 998 is mounted on the lower surface 990 of the bottom flange 970 of the bobbin 966 and is retained in place by a pair of integrally formed projections which project into an aperture formed in the bottom flange 970 and are then flared outwardly in the manner previously described in connection with the primary embodiment of the invention. The contact spring 998 is generally semi-circular in configuration and includes a portion 988 on to which a lead 1000 is connected. The contact spring 998 is formed so that the lower surface 1100 of the contact spring 998 is continuously in contact with the upper surface 1112 of the armature 840 throughout the entire range of motion of the armature 840.

Figure 3:
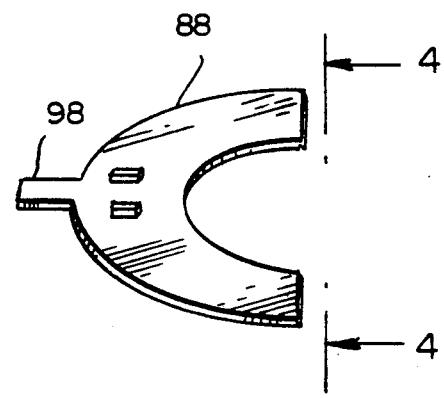
FIG. 3 is a perspective view of the spring contact member shown removed from the solenoid control valve of FIG. 1.
Figure 4:
FIG. 4 is an end view of the spring contact member taken along line 4—4 of FIG. 3.
Figure 5:
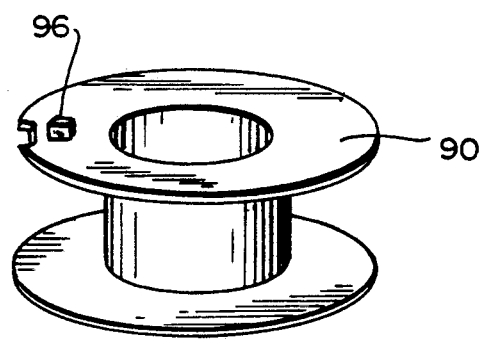
FIG. 5 is a perspective view of the solenoid bobbin shown removed from the solenoid control valve of FIG. 1.

The contact spring 998 and the bobbin 966 are identical to the contact spring 88 and the bobbin 66 which were previously shown in FIGS. 3-5 and which were described in connection with the primary embodiment of the invention.

An insulating disk 1114 is positioned below the armature 840 between the armature 840 and the top plate 804, thereby electrically insulating the armature 840 from the top plate 804. The insulating disk 1114, as previously described, may be made of Mylar or any similar thin sheet plastic material which has good electrical insulating properties. The armature 840 is mounted on the shaft 838 which, as previously indicated, is also an electrical insulator and consequently the armature 840 is completely insulated from the solenoid housing 846 except in the critical manner which will be presently described.

When the solenoid coil 854 is energized, the armature 840 moves upward in the direction indicated by the arrow 1118 in FIG. 11 until the top surface 1112 rests against the surface 1120 of an armature stop portion 1122 which is integrally formed in the solenoid housing 846. When the armature 840 moves upward, the poppet 836 moves away from the valve seat 824 and contact between the armature 840 and the solenoid housing 846 completes a circuit between the lead 1124 which is connected to the solenoid housing 846 and the lead 1000 which is connected to the contact spring 998.

When the solenoid coil 854 is deenergized, the helical spring 842 forces the armature 840 away from the armature stop portion 1122, thereby breaking the electrical connection between the leads 1000, 1124. The helical spring 842 forces the armature 840 toward the top plate 804. However, the insulating disk 1114 prevents electrical contact between the armature 840 and the top plate 804 while the poppet 836 is in contact with the valve seat 824.

The action of the armature 840 to make and break the electrical circuit formed by the leads 1000, 1124 provides a precise electrical indication of the mechanical position of the solenoid control valve 800. This electrical indication of the mechanical position of the solenoid control valve 800 is provided without a need to resort to external sensor assemblies, sliding contacts or other devices which are subject to errors caused by mechanical hysteresis and wear.

Although the solenoid control valves according to the present invention have been described as controlling fluids, it should be understood that these valves may also be used for controlling gases.

While preferred embodiments of the invention have been shown and described herein, it is obvious that numerous additions, changes and omissions may be made in such embodiments without departing from the spirit and scope of the invention.

What is claimed is:

1. A solenoid control valve comprising:
    a valve body,
    fluid control means disposed in said valve body, and comprising diaphragm and poppet means,
    electrically operated solenoid means mounted on said valve body with said solenoid means comprising a solenoid housing, a solenoid coil, a solenoid bobbin, and an armature disposed for actuation by said solenoid means,
    electrical switch means having a fixed portion and a moveable portion with said fixed portion comprising said solenoid housing and with said moveable portion comprising said armature,
    actuation means connected to said armature for actuation of said fluid control means respective to the position of said armature,
    electrical connection means continuously providing electrical contact with said armature means, and
    mechanical stop means formed in said solenoid housing with said armature means making electrical and mechanical contact with said mechanical stop means at one end of its travel.

2. A solenoid control valve according to claim 1 in which said electrical connection means further comprises
    leaf spring contact means having a first end, and a second end with said first end mounted on said solenoid bobbin means and with said second end bearing on said armature.

3. A solenoid control valve according to claim 1 further comprising
    first electrical lead means connected to said electrical connection means, and
    second electrical lead means connected to said solenoid housing.

4. A solenoid control valve according to claim 1 in which said solenoid bobbin is made of a non-conductive material.

5. A solenoid control valve according to claim 2 in which said leaf spring contact has a semi-circular configuration.

6. A solenoid control valve according to claim 1 in which said actuation means connected to said armature are made of a non-conductive material.

7. A solenoid control valve according to claim 1 further comprising insulating means interposed between said armature and said solenoid housing.

8. A solenoid valve according to claim 7 in which said insulating means comprises a sheet of insulating film.

9. In a solenoid activated valve having an armature, an electrically conductive solenoid housing and a solenoid bobbin, a method for sensing switch position comprising:

electrically insulating said armature from said solenoid housing, providing an electrical connection means continuously connected to said armature, with said electrical connection means insulated from said solenoid housing, said electrical connection means comprising a leaf spring contact having a first end and a second end, said first end being mounted on said solenoid bobbin and said second end bearing on said armature, and allowing contact between said armature and said solenoid housing at the end of an armature stroke, thereby closing an electrical circuit between said electrical connection means and said solenoid housing.

10. In a solenoid activated valve having an armature, an electrically conductive solenoid housing and a solenoid bobbin, the method for sensing solenoid position according to claim 9 in which said step of electrically insulating said armature from said solenoid housing further comprises:

interposing an insulating layer between said armature and said solenoid housing.

11. In a solenoid activated valve having an armature, an electrically conductive solenoid housing and a solenoid bobbin, a method for sensing armature position according to claim 9 in which said step of electrically insulating said armature from said solenoid housing further comprises:

mounting said armature on an insulated actuator shaft.

12. A solenoid control valve comprising:

a valve body, fluid control means disposed in said valve body, electrically operated solenoid means mounted on said valve body with said solenoid means comprising a solenoid housing, a solenoid coil, a solenoid bobbin, and an armature disposed for actuation by said solenoid means, electrical switch means having a fixed portion and a moveable portion with said fixed portion comprising said solenoid housing and with said moveable portion comprising said armature, actuation means connected to said armature for actuation of said fluid control means respective to the position of said armature, electrical connection means continuously providing electrical contact with said armature means, said electrical means comprising a leaf spring contact having a first end and a second end with said first end being mounted on said solenoid bobbin and with said second and bearing on said armature, and mechanical stop means formed in said solenoid housing with said armature means making electrical and mechanical contact with said mechanical stop means at one end of its travel.

* * * * *